(12) United States Patent
Cormier et al.

(10) Patent No.: US 10,323,763 B2
(45) Date of Patent: Jun. 18, 2019

(54) CHECK VALVE HAVING POLYMERIC SEAT AND POPPET

(71) Applicant: Waters Technologies Corporation, Milford, MA (US)

(72) Inventors: Sylvain Cormier, Mendon, MA (US); Joshua A. Shreve, Franklin, MA (US)

(73) Assignee: WATER TECHNOLOGIES CORPORATION, Milford, MA (US)

( * ) Notice: Subject to any disclaimer, the term of this patent is extended or adjusted under 35 U.S.C. 154(b) by 355 days.

(21) Appl. No.: 14/907,857

(22) PCT Filed: Jul. 30, 2014

(86) PCT No.: PCT/US2014/048847
§ 371 (c)(1),
(2) Date: Jan. 27, 2016

(87) PCT Pub. No.: WO2015/017523
PCT Pub. Date: Feb. 5, 2015

(65) Prior Publication Data
US 2016/0178078 A1    Jun. 23, 2016

Related U.S. Application Data

(60) Provisional application No. 61/859,916, filed on Jul. 30, 2013.

(51) Int. Cl.
*F16K 25/00* (2006.01)
*F04B 53/10* (2006.01)
(Continued)

(52) U.S. Cl.
CPC ............ *F16K 25/005* (2013.01); *B01D 15/14* (2013.01); *F04B 53/10* (2013.01); *F16K 1/38* (2013.01);
(Continued)

(58) Field of Classification Search
None
See application file for complete search history.

(56) References Cited

U.S. PATENT DOCUMENTS 3,811,470 A    5/1974   Schaefer
4,245,963 A    1/1981   Hutchins et al.
(Continued)

FOREIGN PATENT DOCUMENTS

DE    29609979 U1    10/1997
DE    10243291 A1    4/2004
(Continued)

OTHER PUBLICATIONS

International Search Report & Written Opinion in International Patent Application No. PCT/US14/48847, dated Nov. 24, 2014; 9 pages.
(Continued)

*Primary Examiner* — Richard C Gurtowski
(74) *Attorney, Agent, or Firm* — Schmeiser, Olsen & Watts LLP

(57) ABSTRACT

A check valve comprises a valve seat element along a fluid path that is formed of a polymeric material and comprises a hole that extends from an input end of the valve seat element to an output end of the valve seat element. The valve seat element includes an inner taper that transitions the input end to the output end, the valve seat element including a sealing surface along the inner taper. A poppet body is formed of a polymeric material and configured to engage the internal tapered sealing surface of the valve seat element. The poppet body moves between a first position at which the poppet body sealingly engages the tapered sealing surface of the valve seat element and a second position at which the poppet body is separate from the inner taper of the valve seat member.

20 Claims, 7 Drawing Sheets

(51) Int. Cl.
  *F16K 1/38*    (2006.01)
  *F16K 15/02*   (2006.01)
  *B01D 15/14*   (2006.01)
  *F16K 15/06*   (2006.01)
  *G01N 30/36*   (2006.01)
  *G01N 30/26*   (2006.01)
  *G01N 30/32*   (2006.01)

(52) U.S. Cl.
  CPC .......... *F16K 15/026* (2013.01); *F16K 15/063* (2013.01); *G01N 30/26* (2013.01); *G01N 30/36* (2013.01); *G01N 2030/328* (2013.01)

(56) References Cited

U.S. PATENT DOCUMENTS

| | | | |
|---|---|---|---|
| 4,850,393 A | 7/1989 | Lashomb | |
| 4,867,200 A | 9/1989 | Markley | |
| 2003/0037822 A1 | 2/2003 | Fischer et al. | |
| 2003/0047216 A1 | 3/2003 | Kelly | |
| 2010/0158704 A1 | 6/2010 | Charlton et al. | |
| 2012/0118406 A1 | 5/2012 | Edgeworth | |
| 2012/0132841 A1* | 5/2012 | Aoki | F01L 1/462 251/337 |

FOREIGN PATENT DOCUMENTS

| | | |
|---|---|---|
| JP | 317214 Y1 | 5/1956 |
| JP | 5576964 U | 5/1980 |
| JP | 2001182852 A | 6/2001 |
| JP | 2002113100 A | 4/2002 |
| JP | 2011027046 A | 10/2011 |
| WO | 2013134215 A1 | 9/2013 |

OTHER PUBLICATIONS

International Preliminary Report on Patentability in International Patent Application No. PCT/US14/48847, dated Feb. 11, 2016; 8 pages.
Extended Search Report in counterpart European Patent Application No. 14832346.2, dated Feb. 17, 2017; 9 pages.
Office Action in counterpart Japanese Patent Application No. 2016-531855, dated Jul. 3, 2018; 9 pages.

\* cited by examiner

CHECK VALVE HAVING POLYMERIC SEAT AND POPPET

RELATED APPLICATIONS

This application claims priority to and the benefit of the filing date of U.S. Provisional Application Ser. No. 61/859,916, filed Jul. 30, 2014, titled "CHECK VALVE HAVING POLYMERIC SEAT AND POPPET", the entirety of which is incorporated herein by reference.

FIELD OF THE INVENTION

The invention relates generally to a check valve. More particularly, the invention relates to a check valve for high pressure fluid flows such as in a high pressure liquid chromatography system.

BACKGROUND

Instruments used in analytical and preparative chemistry often include valves to control the flow of fluids. Check valves are one important class of flow-control valves, and are typically utilized to permit fluid flow in one direction, while impeding fluid flow in the reverse direction. Chromatography applications, for example, typically include check valves in fluid communication with respective inlet and outlet ports of a displacement pump to control the direction of fluid flow through the pump.

For example, U.S. Pat. No. 3,810,716 to Abrahams et al. ("Abrahams") illustrates inlet and outlet check valves applied to a high-pressure chromatography reciprocating two-piston pump. The pump employs an inlet and an outlet check valve respectively on each of two displacement chambers or cylinders. The pump has a "parallel" configuration, which delivers fluid to a downstream receiving system alternately from the two pump cylinders; each cylinder is in direct fluid communication with the receiving system during a portion of the pump cycle. The alternating pattern of fluid delivery allows one pump cylinder to be refilled while delivery from the other pump cylinder sustains the desired pump output flow rate to the downstream system.

The inlet and outlet check valves associated with each cylinder in this parallel configuration allow each cylinder to communicate either with an inlet fluid pathway from a solvent reservoir or with an outlet fluid pathway to the downstream receiving system. The operation and location of the check valves substantially prevents the backflow of fluid from the pressurized system into a pump cylinder that is undergoing refill at substantially atmospheric pressure.

Another common configuration of a high-pressure pump for liquid chromatography is a "serial" configuration, illustrated for example in U.S. Pat. No. 4,245,963 to Hutchins et al. Here, liquid inspired at a pump intake is directed serially through a first pump cylinder and a second pump cylinder. Only a single inlet and a single outlet check valve are utilized. The coordinated motion of respective first and second pistons interacts cooperatively with the actions of the inlet and the outlet check valves to achieve a substantially constant output flow rate of liquid to a downstream receiving system.

As with the parallel pump configuration, a single drive motor may be used to affect the coordinated motion of the two pistons, through use of appropriate gearing or equivalent drive elements. Alternatively, a separate motor may be allocated for the drive of each piston, which can allow greater operational flexibility in motion coordination.

A ball-and-seat type of chromatography-pump check valve is particularly common. A typical configuration employs a stationary seat and a ball that is capable of being displaced toward or away from the seat. In a passive ball-and-seat check valve, fluid flow in one direction urges the ball against the seat, blocking the flow of fluid. Fluid flow in the opposite direction urges the ball away from the seat, opening a pathway through the valve. Some passive check valves include a spring that holds the ball against the seat until a differential fluid pressure across the valve exceeds a threshold value as determined by the force applied by the spring.

A chromatography pump check-valve ball is commonly fabricated from ruby while a check-valve seat is commonly fabricated from sapphire, zirconia, ruby, or materials that include crystalline aluminum oxide. Alternatively, check-valve balls and seats are fabricated from, for example, aluminum-oxide based ceramics, due to certain desired properties, for example, for their chemical inertness, resistance to wear, machineability, and/or stiffness.

Chromatography pumps are generally high-precision devices, designed to produce substantially stable and reproducible solvent flows at delivery pressures of as much as thousands of pounds per square inch (psi) or greater (i.e., tens of megaPascals or greater.) Back-leakage of a check valve can degrade or destroy the desired relationship between a control input (such as a pump step-motor step rate or step count) and a volume delivery output of chromatography solvent. As liquid chromatography systems for higher pressures and lower flow rates have been developed, attention has been directed to reducing leak rates. To achieve this goal, considerable effort has been expended by check valve manufacturers to produce balls that are highly spherical and that have an excellent surface finish. A corresponding effort has been expended by manufacturers to produce seats having a spherical sealing surface with a close tolerance as well as an excellent surface finish. The machining and grinding processes used for improved surface finishes and tight tolerances result in increased costs.

Many existing valves such as the abovementioned check valve including from a ruby ball and sapphire seat, though providing a good seal when new, become fouled in service by contamination such as foreign matter that lodges on either the ball or the seat sealing surface. This fouling at times is transient, where the fouling substance is swept downstream on a subsequent valve actuation, or may be more permanent, where restoration of proper valve function may require valve disassembly and aggressive cleaning, or component replacement. While fouling matter resides on the ball or seat, the check valve may be rendered partially or wholly inoperable due to a failure to properly seal against reverse flow. In another failure mode, the ruby and sapphire materials may become stuck together in the presence of particular solvents, rendering the valve inoperable because it cannot enable fluid flow in the forward direction.

Filters of various types have been employed by chromatography pump manufacturers in attempts to eliminate at least certain classes of particulate fouling. In practice, however, an in-line solvent filtration device that could remove all or nearly all incoming particulate contamination would typically require an effective pore size so small that the pump intake can become starved.

SUMMARY

In one aspect, the invention features a check valve for a chromatography system. The check valve comprises an inlet at a first end of the check valve; an outlet at a second end of the check valve and a fluid path extending between the inlet and the outlet. The check valve also comprises a valve seat element along the fluid path. The valve seat element is formed of a polymeric material and comprises a hole that extends from an input end of the valve seat element to an output end of the valve seat element. The valve seat element further includes an inner taper that transitions the input end to the output end, the valve seat element including a sealing surface along the inner taper. The check valve also includes a poppet body formed of a polymeric material and configured to engage the internal tapered sealing surface of the valve seat element. The poppet body is configured for a movement between a first position at which the poppet body sealingly engages the tapered sealing surface of the valve seat element and a second position at which the poppet body is separate from the inner taper of the valve seat member.

In another aspect, the invention features a chromatography solvent delivery system, comprising: at least one pump and at least one check valve in communication with at least one of an input region and an output region of the at least one pump. The at least one check valve comprises an inlet at a first end of the check valve; an outlet at a second end of the check valve a fluid path extending between the inlet and the outlet; a valve seat element along the fluid path, the valve seat element formed of a polymeric material and comprising a hole that extends from an input end of the valve seat element to an output end of the valve seat element, the valve seat element further including an inner taper that transitions the input end to the output end, the valve seat element including a sealing surface along the inner taper; and a poppet body formed of a polymeric material and configured to engage the internal tapered sealing surface of the valve seat element. The poppet body is configured for movement between a first position at which the poppet body sealingly engages the tapered sealing surface of the valve seat element and a second position at which the poppet body is separate from the inner taper of the valve seat member.

In another aspect, the invention features a method for operating a chromatography solvent delivery system, comprising positioning a valve seat element along a fluid path between an input end and an output end of a pump, the valve seat element formed of a polymeric material and including an inner taper; positioning a poppet body formed of a polymeric material at a first position where the poppet body sealingly engages the inner taper of the valve seat element; and transitioning the poppet body to a second position in response to a flow a fluid from the inlet, the second position at which the poppet body is separate from the inner taper of the valve seat member.

BRIEF DESCRIPTION OF THE DRAWINGS

The above and further advantages of this invention may be better understood by referring to the following description in conjunction with the accompanying drawings, in which like reference numerals indicate like elements and features in the various figures. For clarity, not every element may be labeled in every figure. The drawings are not necessarily to scale, emphasis instead being placed upon illustrating the principles of the invention.

DETAILED DESCRIPTION

Figure 1A:
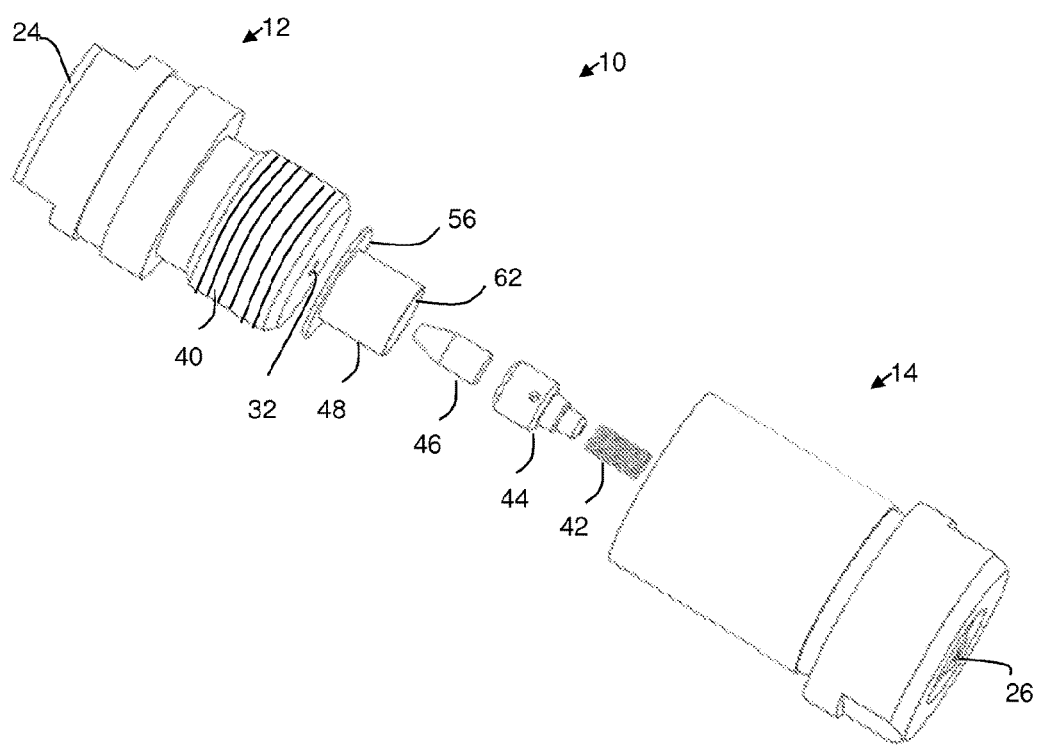
FIG. 1A is an exploded perspective view of a check valve, in accordance with an embodiment.

Reference in the specification to "one embodiment" or "an embodiment" means that a particular, feature, structure or characteristic described in connection with the embodiment is included in at least one embodiment of the teaching. References to a particular embodiment within the specification do not necessarily all refer to the same embodiment.

The present teaching will now be described in more detail with reference to exemplary embodiments thereof as shown in the accompanying drawings. While the present teaching is described in conjunction with various embodiments and examples, it is not intended that the present teaching be limited to such embodiments. On the contrary, the present teaching encompasses various alternatives, modifications and equivalents, as will be appreciated by those of skill in the art. Those of ordinary skill having access to the teaching herein will recognize additional implementations, modifications and embodiments, as well as other fields of use, which are within the scope of the present disclosure as described herein.

In brief overview, the invention relates to a check valve having a valve seat and a corresponding poppet that engages with and disengages from the valve seat, for example, to control an output of an eluent during an operation. A first opening at a first end of the check valve can receive a flow of fluid such as a sample from a source. The check valve includes a fluid path that extends from the first opening to a second opening at an opposite end of the check valve. The second opening can output a fluid to a pump or other chromatography-related device. The valve seat and corresponding poppet are positioned along the fluid path. The valve seat element is preferably formed of a polymeric material, for example, including polyimide, or related material having an elastic property. The poppet can likewise be formed of a polymeric material, but that has a hardness greater than that of the valve seat.

The valve seat element further comprises a hole that extends from an input end of the valve seat element to an output end of the valve seat element. The hole in the valve seat element further includes an inner taper. The inner taper on the seat provides a sealing surface for the poppet, it also avoids line contact between the two components to prevent excessive deformation at the contact area. The poppet is configured for movement between a first position at which the surface of the poppet engages a sealing surface at the inner taper of the valve seat member and a second position at which the poppet is separate from the inner taper of the valve seat member. A sufficient force can be applied against the inner taper when the poppet is in the first position so that the valve seat member can be compressed against, and compliantly conform with, the poppet to restrict a flow of fluid at the interface between the poppet and the valve seat member. The poppet can transition to the second position where the poppet is separated from the inner taper. The compliant inner taper of the valve seat member can return to its original shape, i.e., prior to temporary deformation of the inner taper caused by the interfacing of the poppet and the inner taper. When the poppet is separate from the inner taper, a flow of fluid can occur through the hole from the input end of the valve seat element to the output end of the valve seat element.

As used herein, "compliance" means the ability of an object to yield elastically when a force is applied to the object. The compliance of both the polymeric seat and the polymeric poppet results in a check valve that is more rugged than a conventional ball and seat check valve. The check valve seals better at higher pressures because the sealing surfaces of the polymeric seat and polymeric poppet adapt to each other as the pressure increases. The check valve can be manufactured with reduced tolerances and small imperfections introduced during the manufacturing process can be tolerated. Moreover, the compliance of the two components permits a seal to form around small contaminants or fouling material that might otherwise lodge on the sealing surface of either component during operation, for example, in conventional applications that include O-rings or other standalone seals that are glued or otherwise bonded between valve elements. Also, the polymeric seat/polymeric poppet relationship is advantageous at higher pressures due to the relatively high compliance as compared to ceramics or related materials. In particular, ceramic check valves are well-known for performing poorly at pressure deltas below 1000 psi.

Figure 1B:
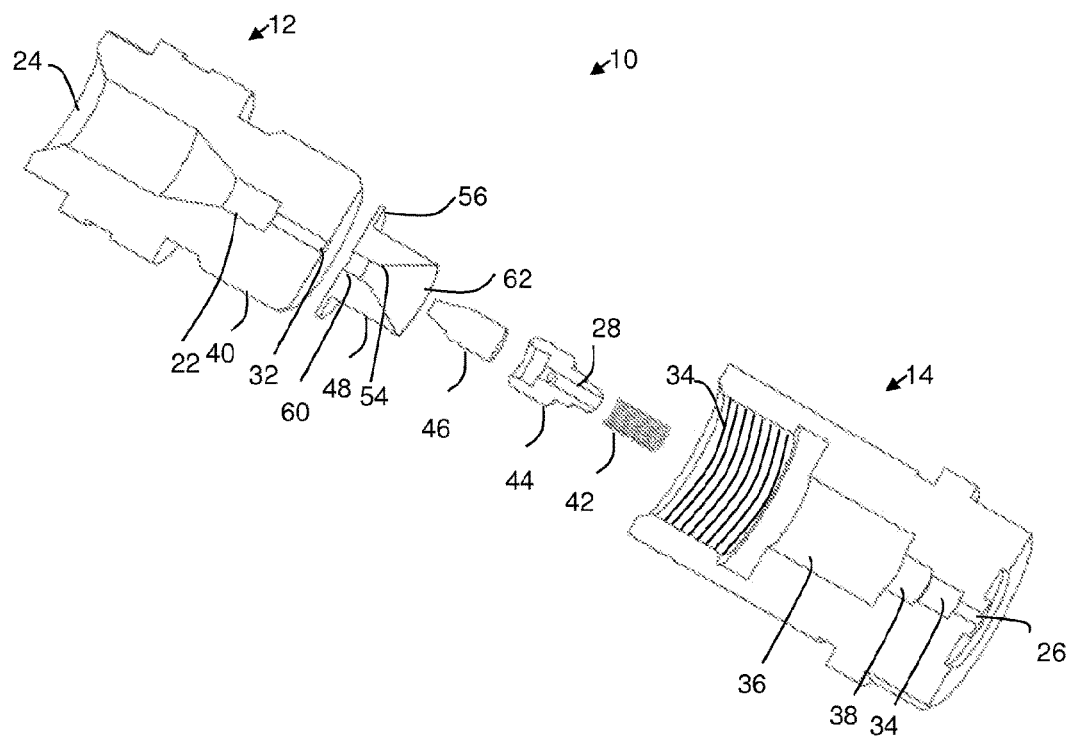
FIG. 1B is an exploded cross-sectional view of the check valve of FIG. 1A.

FIG. 1 is a cross-sectional illustration of a check valve 10 according to one embodiment of the invention. The check valve 10 can be a pump inlet check valve or an outlet check valve, for example, when constructed and arranged to be in parallel, for example, shown in FIG. 4. In other embodiments, the check valve can include a primary and/or accumulator check valve, for example, constructed and arranged serially, for example, shown in FIG. 5. The valve 10 includes a first valve body portion 12 and a second valve body portion 14, collectively referred to herein as the valve body. The valve body portions 12, 14 can be secured to each other via a threaded surface on the first valve body portion that engages a threaded inner surface region of the second valve body portion.

A first fluid channel 22 extends axially through the first valve body portion 12 from an inlet 24 at an external end of the first valve body portion 12 to an outlet 32 of the first valve body portion 12. The external end is configured to receive a coupling to thereby couple the first fluid channel 22 to tubing or a system component. For example, the first fluid channel 22 can be coupled to an output of a liquid chromatography system component such as a high pressure liquid chromatography pump.

Figure 1C:
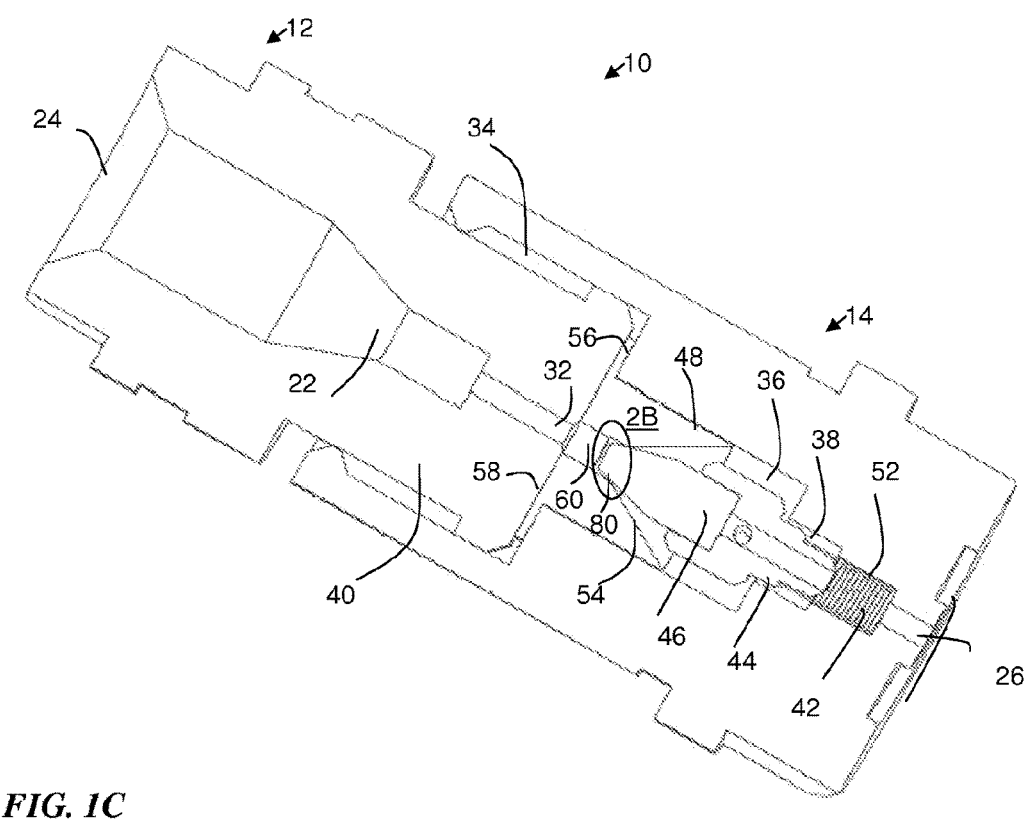
FIG. 1C is a cutaway assembled perspective view of the check valve of FIGS. 1A and 1B.

The second valve body portion 14 includes a hole that extends axially from an opening 36 at an external end of the second valve body portion 14 to an outlet 26 of the second valve body portion 14. The hole includes a first region 34, a second region 36, a third region 38, a fourth region 52, and a fifth region or outlet 26. The first through fifth regions 34, 36, 38, 52, and 26 can have different diameters, widths, surface areas, or other dimensions. The opening at the first region 34 can be threaded for receiving the body portion 40, which can likewise be threaded. As shown in FIG. 1C, the first region 34 can receive and engage with a body portion 40 of the first valve body portion 12. A compression spring 42, a poppet holder 44, poppet body 46, and a first portion of the seat element 48 can be positioned inside the second region 36. The poppet holder 44 transitions the poppet body 46 between a first position at which the poppet body 46 engages the tapered sealing surface 54 of the valve seat element 48 to permit fluid to flow from the inlet to the outlet, but to impede or restrict a flow from the outlet to the inlet, and a second position at which the poppet body 46 is separate from the inner taper 54 of the valve seat member 48. In an embodiment, the poppet holder 44 and the poppet body 46 are formed of a single integrated unit, for example, formed from a single stock. In another embodiment, the poppet holder 44 and the poppet body 46 are physically distinct elements. A second portion of the seat element 48 can be positioned in the third region 38. A first portion of the spring 42 can also be positioned in the third region 38, and a second portion of the spring 42 can be positioned in the fourth region 52. A fluid path can be formed from the first through fifth regions 34, 36, 38, 52, and 26, regardless of the presence of the abovementioned elements in one or more regions 34, 36, 38, 52, and 26. At least the first region 34 and the fourth region 52 can include a counterbore.

The compression spring 42 can be positioned along the fluid path, and can be coupled to the poppet holder 44 between the poppet body 46 and the outlet 26. The spring 42 can exert a predetermined force on the poppet body 46 via the poppet holder 44. The poppet body 46, in turn, can exert a force on the seat element 48. The spring 42 therefore assists in placing the poppet body 46 in a closed state when abutting the seat element 48. In an embodiment, the check valve 10 is adjustable, for example, by including an adjusting screw acting on the spring 42 that can be compressed or decompressed so that the valve 10 can be set to open at any pressure within a desired range, for example, whereby the spring 42 permits the poppet body 46 to enter an open state at about a 1-2 psi delta. The spring force can be a minimal force, permitting any non-zero fluid pressure to be sufficient to achieve flow through the check valve.

The seat element 48 includes a tapered, funnel-shaped, or conical fluid path 54 that extends from a first opening 60 at an input end of the seat element 48 to a fluid path 28 in the poppet holder 44 at a second opening 62 of the seat element 48. The second opening 62 is configured to receive the poppet body 46. A first portion of the poppet body 46 can abut the inner taper 54 of the seat element 48, for example, due to the force applied by the spring 42. A second portion of the poppet body 46 can be coupled to the poppet holder 44, which moves in response to a motion of the spring 42. Accordingly, the spring 42 can hold the poppet body 46 tightly seated at the taper 54, for example, in the abovementioned closed state. A seal is therefore provided between the body 46 and the seat element 48 by pressure acting on the poppet body 46 so as to provide so as to restrict or prevent a flow of fluid, and obviating the use of O-rings or the like. When fluid pressure against the poppet body 46 at the opening 60 is greater than a force imparted on an opposite end of the poppet body 46, for example provided by the spring 42, the poppet body 46 can be separated from the taper 54, and the fluid can flow through. When fluid pressure against the poppet body 46 at the opening 60 is less than a force imparted on an opposite end of the poppet body 46, the force imparted by the spring 42 can cause the poppet body 46 to move against the taper 54 and stop the flow. In order to re-open the valve 10, the pressure-induced force must be sufficient to move the poppet body 46 away from the taper 54, for example, at or about a 1-2 psi delta. Also, the force can overcome an undesirable adhesion force that may occur between the poppet 46 and the seat element 48. In an embodiment, the check valve 10 functions as a flow restrictor to prevent a fluid flow direction in the opposite direction.

In an embodiment, the seat element 48 is formed of a polymeric material such as polyimide. The poppet body 46 can also be formed of a polymeric material such as polyimide, or zirconia, sapphire, metal, or a combination thereof and/or other materials. In an embodiment, the hardness of the polymeric material forming the poppet body 46 is greater than the hardness of the polymeric material forming the seat element 48, such that the seat element 48 is softer or more compliant than the poppet 46, which can prevent or mitigate deformation of the poppet 46. In other embodiments, the poppet body 46 and the seat element 48 are formed of different materials, and one of the poppet body 46 and the seat element 48 is formed of a material that is compliant relative to the material forming the other of the poppet body 46 and the seat element 48. In an embodiment, Accordingly, the seat element 48 can compliantly deform when abutting the poppet body 46. In another embodiment, the hardness of the polymeric material forming the poppet body 46 is less than the hardness of the polymeric material forming the seat element 48.

Figure 2A:
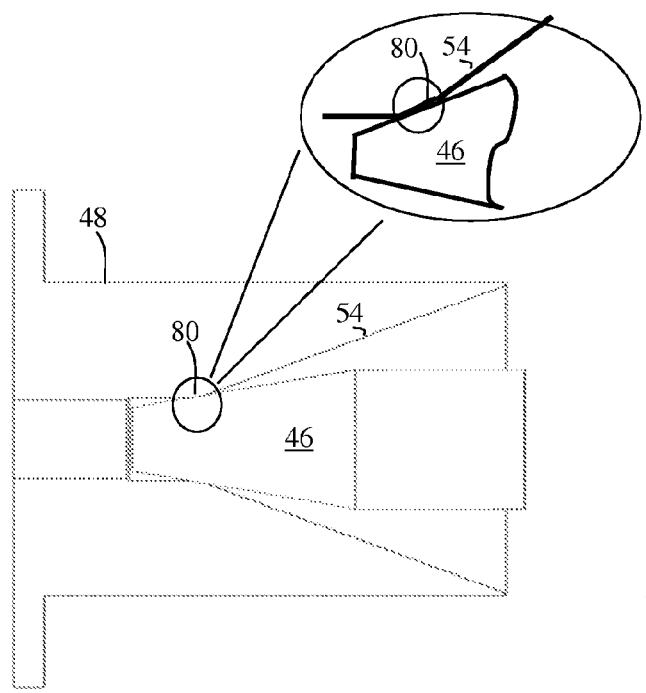
FIG. 2A is a blown-up view of a region of a check valve illustrating a poppet and seat in an closed state.
Figure 2B:
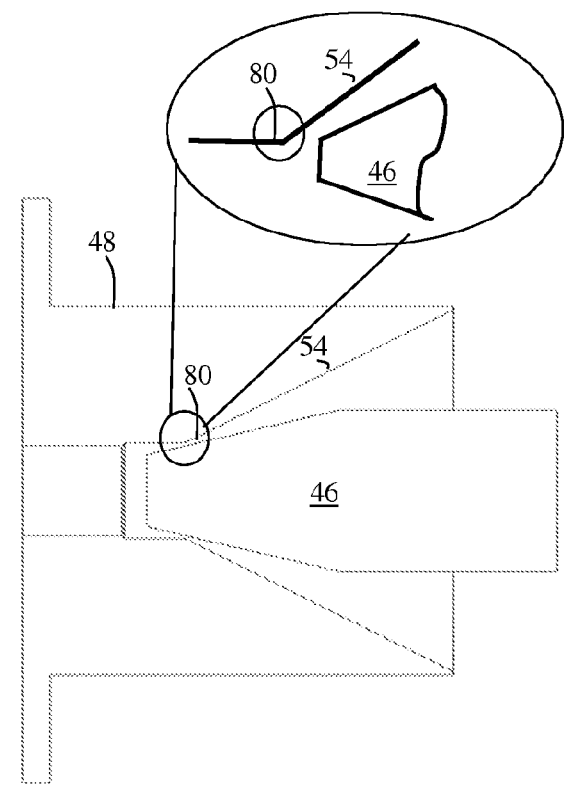
FIG. 2B is a blown-up view of a region of a check valve illustrating a poppet and seat in a open state.

For example, as shown in FIG. 2A, when a force is applied, for example, by the spring 42, against the poppet body 46, the surface of the poppet body 46 can abut the seat element 48 such that at least a portion of the seat element 48 is deformable, shown in FIG. 2A at region 80, relative to the poppet body 46 to form a fluid-tight seal or interface at the region 80 between the poppet body 46 and the seat element 48. The seat element 48 can include an elastic characteristic. As shown in FIG. 2B, the poppet body 46 can be separated from the seat element 48, for example, whereby fluid pressure against the poppet body 46 by fluid received at the inlet 24 and flowing in the direction toward the outlet 26 can result in a depression of the spring 42, whereby the poppet body 46 moves away from the seat 48. Here, the region 80 of the seat element 48 formally part of the interface can return to a state prior to interfacing with the poppet body 46. The tapered fluid path 54 is opened, and the fluid can flow along the fluid path in the second valve body portion 14 for output from the outlet 26. When fluid pressure is reduced or ceased, the spring 42 reseats the poppet body 46 against the seat element 48 as shown in FIG. 2A.

Returning to FIGS. 1A-1C, the seat element 48 includes a sealing flange 56 at an end of the seat element 48. The sealing flange 56 has a width or diameter that is greater than that of the seat element body 48. The sealing flange 56 and the seat element 48 can be formed from a single material stock. Alternatively, the sealing flange 56 can be formed separately from the seat element body 48 and bonded, glued, or otherwise coupled to the seat element body 48. A single component is preferable as it limits the number of sealing surfaces required. When the check valve 10 is assembled, as shown in FIG. 1C, the sealing flange 56 abuts the surface 58 of the first valve body portion 12 about the outlet 32, and provides a fluid-tight seal between the first and second valve body portions 12, 14. In particular, the first valve body portion 12 can be coupled to, for example, threaded into, the second valve body portion 14 with a force that is sufficient to provide a fluid-tight seal or interface at the sealing flange 56 between the first and second valve body portions 12, 14. In an embodiment, the rotational torque between the first valve body portion 12 and the first region 34 of the second valve body portion 14, for example, in threads in the first region 34, translates to a force, which can deform the sealing flange 56 to form the interface, similar to the seal-tight interface 80 formed between the poppet 46 and the seat element 48 described with reference to FIGS. 1-2.

The first valve body portion outlet 32 is aligned with the first opening 60 in the seat element 48 sealingly abutting the surface 58 of the first valve body portion 12 to form a fluid path extending from the inlet 24 at the first valve body portion 12 to the outlet 26 of the second valve body portion 14, and including the first fluid channel 22, the first valve body portion outlet 32, the seat element fluid path 54, and the hole in the second valve body portion 14.

The check valve 10 having a polymeric seat and poppet configuration permits the check valve 10 to be rugged as compared to a conventional ball and seat check valve. Also, the check valve 10 seals better at higher pressures because the sealing surfaces of the polymeric seat and poppet adapt to each other as the pressure increases. The check valve can be manufactured with reduced tolerances and small imperfections introduced during the manufacturing process can be tolerated. Moreover, the compliant relationship of the polymeric seat and poppet permits a seal to form around small contaminants or fouling material that might otherwise lodge on the sealing surface of either component during operation, thereby preventing or reducing fluid leaks or the like.

Figures 3A, 3B:
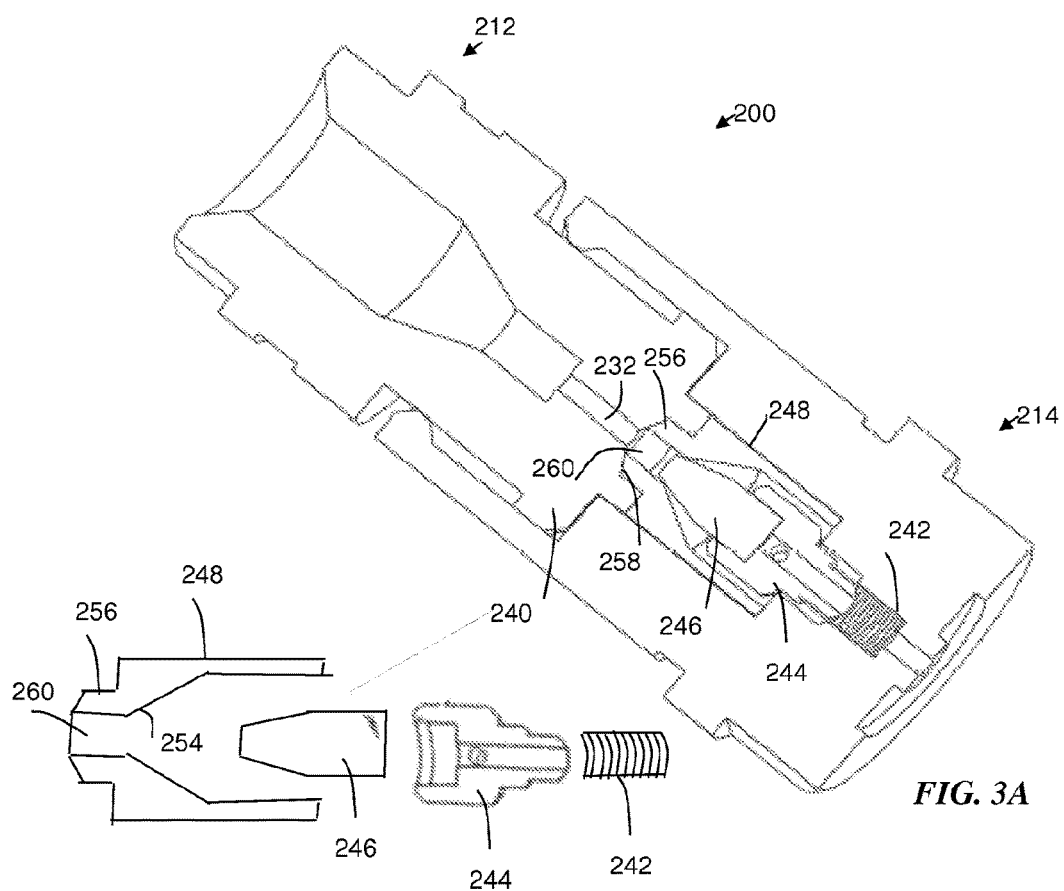
FIG. 3A is a cutaway assembled perspective view of a check valve, in accordance with another embodiment.
FIG. 3B is an exploded cross-sectional view of the check valve of FIG. 3A.

FIG. 3A is a cutaway assembled perspective view of a check valve 200, in accordance with another embodiment. FIG. 3B is an exploded cross-sectional view of the check valve 200 of FIG. 3A. The check valve 200 includes a first valve body portion 212 and a second valve body portion 214, which can include elements that are the same as or similar to the first valve body portion 12 and the second valve body portion 14, respectively, of FIGS. 1 and 2, except for differences described as follows.

A region 234 of the second valve body portion 214 can receive and engage with a body portion 240 of the first valve body portion 212. In an embodiment, an outermost end of the first valve body portion 212 includes an opening 258. The check valve 200 can include a seat element 248 having an end portion 256 that extends from the seat element 248 in an axial direction. The end portion 256 can be configured to adapt with the opening 258 in the first valve body portion 212. The end portion 256 can abut the inner surface of the opening 258, and provide a fluid-tight seal between the first and second valve body portions 12, 14. To form a fluid-tight seal using the end portion 256 of the seat element 248, the first valve body portion 212 can be coupled to, for example, threaded by applying a rotational force with, the second valve body portion 214, which can translate to a force, which can deform the seat element 248 so that the end portion 256 conforms with the opening 258 to form a seal-tight interface.

The seat element 248 can communicate with a poppet body 246, a poppet holder 244, and a spring 244, which can be similar to or the same as those described in other embodiments herein. For example, the poppet body 246 can be similar to or the same as the poppet body 45 of FIGS. 1 and 2, and can provide a fluid-tight seal when abutting an inner tapered opening wall 254 of a polymeric seat element 248.

Figure 4:
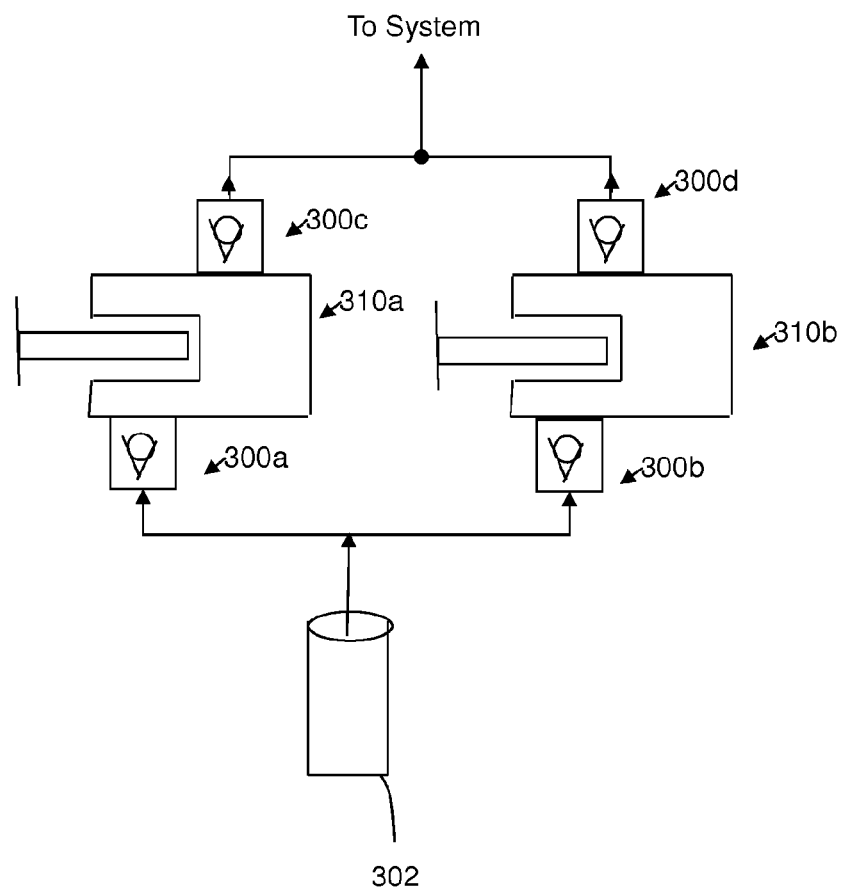
FIG. 4 is a view of a system that includes two pump pistons and four check valves operating in parallel, in accordance with an embodiment.

FIG. 4 is a view of a system that includes two pump pistons 310a, 310b and four check valves 300a-300d operating in parallel, in accordance with an embodiment. The check valves 300a-300d can be similar to the check valves of other embodiments described herein, and therefore will not be repeated for brevity. As shown in FIG. 4, liquid can be output from a solvent reservoir 302 or other fluid source to at least two pump pistons, for example, pump pistons 310a, 310b, of a multi-piston pump. A first inlet check valve 300a is at an inlet side of the first pump piston 310a and a second inlet check valve 300b is at an inlet side of the second pump piston 310b. A first outlet check valve 300c is at an outlet side of the first pump piston 310a and a second outlet check valve 300c is at an outlet side of the second pump piston 310b. The flows of liquid from the first and second output check valves 300c, 300d, respectively, are output to a system, for example, a chromatography column, a mass spectrometer, and/or other chromatography system elements known to those of ordinary skill in the art.

Figure 5:
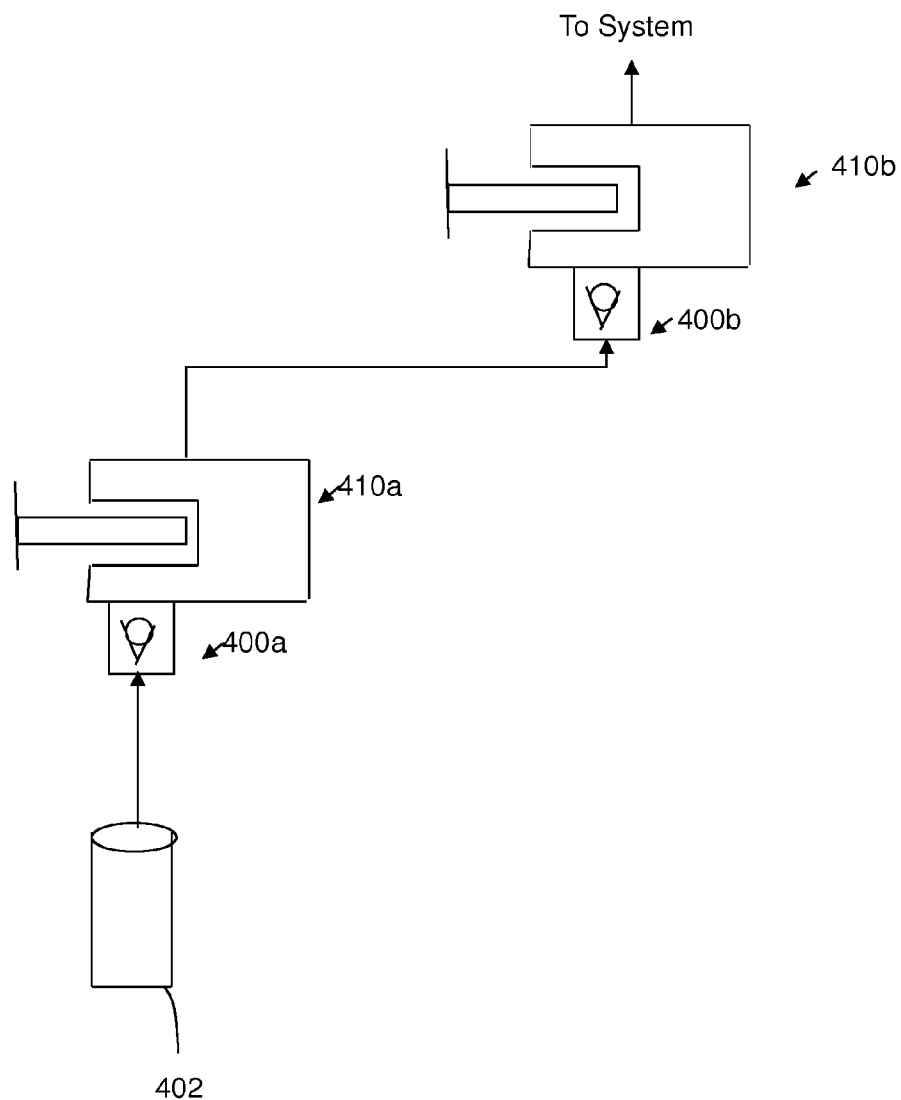
FIG. 5 is a view of a system that includes two pump pistons and two check valves operating serially, in accordance with an embodiment.

FIG. 5 is a view of a system that includes two pump pistons 410a, 410b and two check valves 400a and 400b having a serial configuration, in accordance with an embodiment. The check valves 400a and 400b can be similar to the check valves of other embodiments described herein, and therefore will not be repeated for brevity. As shown in FIG. 5, liquid can be output from a solvent reservoir 402 or other fluid source to at least two pump pistons, for example, pump pistons 310a, 310b, of a multi-piston pump. A first inlet check valve 400a is at an inlet side of the first pump piston 410a. A second inlet check valve 300d is between an outlet side of the first pump piston 410a and an inlet side of the second outlet check valve 400b. The flow of liquid from the source 402 via the first and second output check valves 400a, 400b, respectively, and the first and second pump pistons 410a, 410, respectively, is output to a system, for example, a chromatography column, a mass spectrometer, and/or other chromatography system elements known to those of ordinary skill in the art. Other configurations than those shown in FIGS. 4 and 5, although not shown, are equally applicable.

While the invention has been shown and described with reference to specific embodiments, it should be understood by those skilled in the art that various changes in form and detail may be made therein without departing from the spirit and scope of the invention as recited in the accompanying claims.

What is claimed is:

1. A check valve for a chromatography system, comprising:
   an inlet at a first end of the check valve;
   an outlet at a second end of the check valve;
   a fluid path extending between the inlet and the outlet;
   a valve seat element along the fluid path, the valve seat element formed of a polymeric material and comprising a hole that extends from an input end of the valve seat element to an output end of the valve seat element, the hole of the valve seat element including an opening at the input end, wherein a majority of the hole is funnel-shaped from the opening to the output end, the valve seat element including a sealing surface along the funnel-shaped hole; and
   a poppet body formed of a polymeric material and configured to engage the sealing surface of the valve seat element to form a seal-tight interface at a region of the funnel-shaped hole where the opening of the funnel-shaped hole at the input end of the valve seat element transitions to the funnel-shaped hole, the poppet body configured for movement between a first position at the region of the hole where the seal-tight interface is formed at which the poppet body sealingly engages the sealing surface of the valve seat element and forms a temporary deformation of the funnel-shaped hole and a second position at which the poppet body is separate from the funnel-shaped hole of the valve seat element.

2. The check valve of claim 1, wherein the valve seat element and the poppet body are formed of different polymeric materials.

3. The check valve of claim 2, wherein the valve seat element has a level of compliance that is greater than a level of compliance of the poppet body, and wherein the valve seat element conforms with a surface of the poppet body.

4. The check valve of claim 2, wherein the valve seat element has a level of compliance that is less than a level of compliance of the poppet body, and wherein the poppet body conforms with a surface of the valve seat element.

5. The check valve of claim 1, further comprising a poppet holder that transitions the poppet body from the first position to the second position.

6. The check valve of claim 5, further comprising a spring positioned between the poppet holder and the outlet, and that exerts a spring force on the poppet body, the spring urging the poppet body toward the valve seat element in the absence of a fluid flow in a direction from the inlet toward the poppet body.

7. The check valve of claim 5, further comprising: a first valve body portion that includes the inlet and a second valve body portion that includes the outlet and that is coupled to the first valve body portion.

8. The check valve of claim 7, wherein the valve seat element includes a sealing flange that abuts the first valve body portion, and that provides a fluid-tight interface between the first valve body portion and the second valve body portion.

9. The check valve of claim 1 wherein the poppet body includes a conical end that sealingly engages the funnel-shaped hole of the valve seat element in the first position.

10. The check valve of claim 1 further comprising a valve body having a void therein, the poppet body and poppet disposed in the void and the valve seat disposed at an end of the void with a fluid channel extending from the end of the void at the valve seat and through the valve body.

11. The check valve of claim 1, wherein the polymeric material of at least one of the poppet body and the valve seat element comprises polyimide.

12. A chromatography solvent delivery system, comprising:
    at least one pump; and
    at least one check valve in communication with at least one of an input region and an output region of the at least one pump, the at least one check valve comprising:
      an inlet at a first end of the check valve;
      an outlet at a second end of the check valve;
      a fluid path extending between the inlet and the outlet;
      a valve seat element along the fluid path, the valve seat element formed of a polymeric material and comprising a hole that extends from an input end of the valve seat element to an output end of the valve seat element, the hole of the valve seat element including an opening at the input end, wherein a majority of the hole is funnel-shaped from the opening to the output end, the valve seat element including a sealing surface along the funnel-shaped hole;
      a poppet body formed of a polymeric material and configured to engage the sealing surface of the valve seat element to form a seal-tight interface at a region of the funnel-shaped hole where the opening funnel-shaped hole at the input end of the valve seat element transitions to the funnel-shaped hole, the poppet body configured for movement between a first position at the region of the hole where the seal-tight interface is formed at which the poppet body sealingly engages the sealing surface of the valve seat element and forms a temporary deformation of the funnel-shaped hole and a second position at which the poppet body is separate from the funnel-shaped hole of the valve seat element.

13. The system of claim 12, wherein the valve seat element and the poppet body are formed of different polymeric materials.

14. The system of claim 13, wherein the valve seat element has a level of compliance that is greater than a level of compliance of the poppet body, and wherein the valve seat element conforms with a surface of the poppet body.

15. The system of claim 13, wherein the valve seat element has a level of compliance that is less than a level of compliance of the poppet body, and wherein the poppet body conforms with a surface of the valve seat element.

16. The system of claim 12, further comprising a poppet holder that transitions the poppet body from the first position to the second position.

17. The system of claim 16, further comprising a spring positioned between the poppet holder and the outlet, and that exerts a spring force on the poppet body, the spring urging the poppet body toward the valve seat element in the absence of a fluid flow in a direction from the inlet toward the poppet body.

18. The system of claim 12, wherein the poppet body includes a conical end that sealingly engages the funnel-shaped hole of the valve seat element in the first position.

19. The system of claim 12 further comprising a valve body having a void therein, the poppet body and poppet disposed in the void and the valve seat disposed at an end of the void with a fluid channel extending from the end of the void at the valve seat and through the valve body.

20. A method for operating a chromatography solvent delivery system, comprising:
    positioning a valve seat element along a fluid path between an input end and an output end of a pump, the valve seat element formed of a polymeric material and including a hole including an opening at the input end of the valve seat element, wherein a majority of the hole is funnel-shaped from the opening to the output end, and further includes a sealing surface along the funnel-shaped hole;
    positioning a poppet body formed of a polymeric material at a first position at a region of the funnel-shaped hole where a seal-tight interface is formed where the poppet body sealingly engages the sealing surface of the of the valve seat element and forms a temporary deformation of the funnel-shaped hole; and
    transitioning the poppet body from the first position to a second position in response to a fluid flow from the inlet, the second position at which the poppet body is separate from the funnel-shaped hole of the valve seat element.

* * * * *